United States Patent [19]

Fauchere et al.

[11] Patent Number: 5,569,647
[45] Date of Patent: Oct. 29, 1996

[54] ANGIOPEPTIN CYCLOPEPTIDE COMPOUNDS

[75] Inventors: Jean-Luc Fauchere, Saint-Cloud; Christophe Thurieau, Paris; Jean-Paul Vilaine, Chatenay Malabry; Philip Janiak, Clichy, all of France

[73] Assignee: Adir et Compagnie, Courbevoie, France

[21] Appl. No.: 469,784

[22] Filed: Jun. 6, 1995

Related U.S. Application Data

[63] Continuation of Ser. No. 197,788, Feb. 16, 1994, abandoned.

[30] Foreign Application Priority Data

Feb. 22, 1993 [FR] France ................... 93.01978

[51] Int. Cl.$^6$ ............................. A61K 38/12
[52] U.S. Cl. .................. 514/11; 514/9; 500/11; 500/17; 500/28
[58] Field of Search ............. 514/2, 9, 11; 500/11, 500/17, 28

[56] References Cited

U.S. PATENT DOCUMENTS

| | | | |
|---|---|---|---|
| 4,603,120 | 7/1986 | Kamber | 530/317 |
| 4,650,787 | 3/1987 | Schally et al. | 530/311 |
| 5,147,856 | 9/1992 | Ramwell et al. | 514/16 |
| 5,204,326 | 4/1993 | Fujii et al. | 530/307 |

FOREIGN PATENT DOCUMENTS

| | | | |
|---|---|---|---|
| 180921 | 5/1986 | European Pat. Off. | 530/311 |

OTHER PUBLICATIONS

Amtorp, *Continuous Angiopeptin Infusion Reduces Coronary Restinosis Following Balloon Angioplasty*, Eur. Heart Journal 14, 276 (1993).

McCombe, *Effect of a Long–Acting Somatostatin Analog (BIM23014) on Proliferative Diabetic Retinopathy: A Pilot Study*, Eye 5(5), 569–575 (1991).

Prevost, *Molecular Heterogeneity of Somatostatin Analogue BIM–23014C Receptors in Human Breast Carcinoma Cells Using the Chemical Cross–Linking Assay*, Cancer Research 52(4), 843–850 (1992).

Cotto, *Phase I Study of the Somatostatin Analogue Somatuline in Refractory Small–Cell Lung Carcinoma*, Annals of Oncology 5(3), 290–291 (1994).

Yagoda, *Cytotoxic Chemotherapy for Advanced Hormone–Resistant Prostate Cancer*, Cancer 71(3) Suppl., 1098–1103 (1993).

Venier, *Treatment of Severe Psoriasis with Somatostatin: Four Years of Experience*, Arch. Dermatol. Res. 280 (Suppl), S51–S54 (1988).

Murphy et al, Life Sciences, vol. 40, pp. 2515–2522, (1987).
Schroder et al, The Peptides, vol. 1, pp. 150–151, (1965).

*Primary Examiner*—Howard E. Schain
*Attorney, Agent, or Firm*—The Firm of Gordon W. Hueschen

[57] ABSTRACT

The invention relates to a compound selected from those of formula (I) (SEQ ID NO:1):

$$R_1-X_1-\text{Tyr-D-Trp}-\text{Lys}-\text{Val}-X_2-R_2 \quad (I)$$

(positions 1 2 3 4 5 6 7 8, with a bond between $X_1$ and $X_2$)

in which $R_1$, $R_2$, $X_1$ and $X_2$ are as defined in the description, useful as inhibitor of the proliferation component of vascular smooth muscle cells.

3 Claims, No Drawings

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY: Peptide
        ( B ) LOCATION: 1
        ( D ) OTHER INFORMATION: /label=R1

( i x ) FEATURE:
        ( A ) NAME/KEY: Peptide
        ( B ) LOCATION: 2
        ( D ) OTHER INFORMATION: /label=X1

( i x ) FEATURE:
        ( A ) NAME/KEY: Modified-site
        ( B ) LOCATION: 4
        ( D ) OTHER INFORMATION: /label=D-Trp ( i x ) FEATURE:
        ( A ) NAME/KEY: Peptide
        ( B ) LOCATION: 7
        ( D ) OTHER INFORMATION: /label=X2

( i x ) FEATURE:
        ( A ) NAME/KEY: Peptide
        ( B ) LOCATION: 8
        ( D ) OTHER INFORMATION: /label=R2

( x i ) SEQUENCE DESCRIPTION: SEQ ID NO:1:

Xaa  Xaa  Tyr  Xaa  Lys  Val  Xaa  Xaa
    1                     5

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: circular ( i i ) MOLECULE TYPE: peptide ( i x ) FEATURE:
        ( A ) NAME/KEY: Modified-site
        ( B ) LOCATION: 1
        ( D ) OTHER INFORMATION: /label=H-D-Nal ( i x ) FEATURE:

( A ) NAME/KEY: Peptide
                    ( B ) LOCATION: 4
                    ( D ) OTHER INFORMATION: /label=D- Trp ( i x ) FEATURE:
                    ( A ) NAME/KEY: Peptide
                    ( B ) LOCATION: 7
                    ( D ) OTHER INFORMATION: /label=Dab ( x i ) SEQUENCE DESCRIPTION: SEQ ID NO:2:

Xaa Glu Tyr Xaa Lys Val Xaa Thr
    1               5

( 2 ) INFORMATION FOR SEQ ID NO:3:

( i ) SEQUENCE CHARACTERISTICS:
                    ( A ) LENGTH: 9 amino acids
                    ( B ) TYPE: amino acid
                    ( C ) STRANDEDNESS: single
                    ( D ) TOPOLOGY: circular ( i i ) MOLECULE TYPE: peptide ( i x ) FEATURE:
                    ( A ) NAME/KEY: Modified-site
                    ( B ) LOCATION: 1
                    ( D ) OTHER INFORMATION: /label=H ( i x ) FEATURE:
                    ( A ) NAME/KEY: Peptide
                    ( B ) LOCATION: 5
                    ( D ) OTHER INFORMATION: /label=d- tRP ( i x ) FEATURE:
                    ( A ) NAME/KEY: Peptide
                    ( B ) LOCATION: 8
                    ( D ) OTHER INFORMATION: /label=oRN ( x i ) SEQUENCE DESCRIPTION: SEQ ID NO:3:

Xaa Ala Asp Tyr Xaa Lys Val Xaa Ser
    1               5

( 2 ) INFORMATION FOR SEQ ID NO:4:

( i ) SEQUENCE CHARACTERISTICS:
                    ( A ) LENGTH: 9 amino acids
                    ( B ) TYPE: amino acid
                    ( C ) STRANDEDNESS: single
                    ( D ) TOPOLOGY: circular ( i i ) MOLECULE TYPE: peptide ( i x ) FEATURE:
                    ( A ) NAME/KEY: Modified-site
                    ( B ) LOCATION: 1
                    ( D ) OTHER INFORMATION: /label=H- D-Nal ( i x ) FEATURE:
                    ( A ) NAME/KEY: Modified-site
                    ( B ) LOCATION: 2
                    ( D ) OTHER INFORMATION: /label=homo ( i x ) FEATURE:
                    ( A ) NAME/KEY: Peptide
                    ( B ) LOCATION: 5
                    ( D ) OTHER INFORMATION: /label=D- Trp ( i x ) FEATURE:
                    ( A ) NAME/KEY: Peptide
                    ( B ) LOCATION: 8
                    ( D ) OTHER INFORMATION: /label=Dpr ( x i ) SEQUENCE DESCRIPTION: SEQ ID NO:4:

Xaa Xaa Glu Tyr Xaa Lys Val Xaa Thr
    1               5

( 2 ) INFORMATION FOR SEQ ID NO:5:

( i ) SEQUENCE CHARACTERISTICS:
       ( A ) LENGTH: 8 amino acids
       ( B ) TYPE: amino acid
       ( C ) STRANDEDNESS: single
       ( D ) TOPOLOGY: circular ( i i ) MOLECULE TYPE: peptide ( i x ) FEATURE:
       ( A ) NAME/KEY: Modified-site
       ( B ) LOCATION: 1
       ( D ) OTHER INFORMATION: /label=H- D-Nal ( i x ) FEATURE:
       ( A ) NAME/KEY: Peptide
       ( B ) LOCATION: 2
       ( D ) OTHER INFORMATION: /label=Dab ( i x ) FEATURE:
       ( A ) NAME/KEY: Peptide
       ( B ) LOCATION: 4
       ( D ) OTHER INFORMATION: /label=D- Trp ( x i ) SEQUENCE DESCRIPTION: SEQ ID NO:5:

Xaa  Xaa  Tyr  Xaa  Lys  Val  Glu  Ser
   1                   5

( 2 ) INFORMATION FOR SEQ ID NO:6:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: circular ( i i ) MOLECULE TYPE: peptide ( i x ) FEATURE:
       ( A ) NAME/KEY: Modified-site
       ( B ) LOCATION: 1
       ( D ) OTHER INFORMATION: /label=H ( i x ) FEATURE:
       ( A ) NAME/KEY: Peptide
       ( B ) LOCATION: 3
       ( D ) OTHER INFORMATION: /label=Orn ( i x ) FEATURE:
       ( A ) NAME/KEY: Peptide
       ( B ) LOCATION: 5
       ( D ) OTHER INFORMATION: /label=D- Trp ( x i ) SEQUENCE DESCRIPTION: SEQ ID NO:6:

Xaa  Val  Xaa  Tyr  Xaa  Lys  Val  Asp  Thr
   1                   5

( 2 ) INFORMATION FOR SEQ ID NO:7:

( i ) SEQUENCE CHARACTERISTICS:
       ( A ) LENGTH: 9 amino acids
       ( B ) TYPE: amino acid
       ( C ) STRANDEDNESS: single
       ( D ) TOPOLOGY: circular ( i i ) MOLECULE TYPE: peptide ( i x ) FEATURE:
       ( A ) NAME/KEY: Modified-site
       ( B ) LOCATION: 1
       ( D ) OTHER INFORMATION: /label=H- D-Nal ( i x ) FEATURE:

```
        ( A ) NAME/KEY: Peptide
        ( B ) LOCATION: 2
        ( D ) OTHER INFORMATION: /label=Dpr ( i x ) FEATURE:
        ( A ) NAME/KEY: Peptide
        ( B ) LOCATION: 4
        ( D ) OTHER INFORMATION: /label=D- Trp ( i x ) FEATURE:
        ( A ) NAME/KEY: Modified-site
        ( B ) LOCATION: 7
        ( D ) OTHER INFORMATION: /label=homo ( x i ) SEQUENCE DESCRIPTION: SEQ ID NO:7:

Xaa  Xaa  Tyr  Xaa  Lys  Val  Xaa  Glu  Ser
   1                   5

( 2 ) INFORMATION FOR SEQ ID NO:8:

( i ) SEQUENCE CHARACTERISTICS:
          ( A ) LENGTH: 8 amino acids
          ( B ) TYPE: amino acid
          ( C ) STRANDEDNESS: single
          ( D ) TOPOLOGY: circular ( i i ) MOLECULE TYPE: peptide ( i x ) FEATURE:
          ( A ) NAME/KEY: Modified-site
          ( B ) LOCATION: 1
          ( D ) OTHER INFORMATION: /label=H- D-Nal ( i x ) FEATURE:
          ( A ) NAME/KEY: Peptide
          ( B ) LOCATION: 4
          ( D ) OTHER INFORMATION: /label=D- Trp ( x i ) SEQUENCE DESCRIPTION: SEQ ID NO:8:

Xaa  Cys  Tyr  Xaa  Lys  Val  Cys  Thr
    1                    5
```

ANGIOPEPTIN CYCLOPEPTIDE COMPOUNDS

The present application is a continuation of our prior-filed U.S. application Ser. No. 08/197,788, filed Feb. 16, 1994, and now abandoned.

The present invention relates to new angiopeptin peptide compounds, to a process for the preparation thereof, and to pharmaceutical compositions containing them.

Angiopeptin is an octapeptide amide containing the synthetic amino acids 3-(2-naphthyl)-D-alanine (D-Nal) and D-tryptophan (D-Trp). This octapeptide is partially cyclic, a disulfide bridge connecting the two side chains of the cysteines in positions 2 and 7; it corresponds to the formula (SEQ ID NO:8):

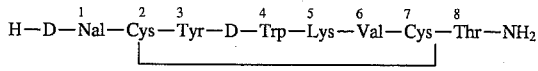

Lundergan et al. (*Atherosclerosis*, 80, 49–55, (1989)) have described for angiopeptin an anti-proliferative effect in vivo on cells of the vascular smooth muscle in a rat carotid artery model involving desiccation of the endothelium in air.

The Applicant has found that the pharmacological properties of angiopeptin could be considerably improved by means of the following two structural modifications:

1)—replacement of the disulfide bridge with an amide bond;

2)—optimisation of the size of the ring by selecting the correct length of the side chains of the amino acid residues on which the ring formation takes place.

The replacement of the disulfide bridge with an amide bond was guided by the fundamental structural differences between these two types of ring formation:

| Disulfide bridge | Amide bond |
| --- | --- |
| non-planar | planar |
| free rotation about the sigma bond | "trans" relative position of the substituents |
| hydrogen bonds impossible | hydrogen bonds possible with other acceptors or donors |

The size of the ring between positions 2 and 7 modifies considerably its configuration as well as the orientation of residues 1 and 8 outside the ring.

The Applicant has found that the compounds having the optimum inhibiting effect with respect to a proliferative vascular lesion are those in which the ring contains 22 atoms.

The compounds of the invention therefore possess pharmacological properties which are superior to those of the analogues hitherto described or claimed. In particular, they inhibit the myointimal proliferation of the rat carotid in vivo more effectively than do angiopeptin or other known analogues.

The invention relates more especially to new peptide compounds corresponding to the general formula (I) (SEQ ID NO:1):

$$R_1-X_1-Tyr-D-Trp-Lys-Val-X_2-R_2 \quad (I)$$
(with a bond connecting $X_1$ and $X_2$, positions 1–8)

in which:

$R_1$ represents an acetylated or non-acetylated, natural or synthetic amino acid residue having the L or D configuration which is commonly used by the person skilled in the art, $R_2$ represents a natural or synthetic amino acid residue having the L or D configuration which is commonly used by the person skilled in the art and the C-terminal function of which is an amide, free acid or alcohol function, $X_1$ and $X_2$ are selected from amino acid residues which permit ring formation by means of an amide bond and which confer on the ring so formed a number of atoms equal to 22, Tyr represents the D-tyrosine residue, D-Trp represents the D-tryptophan residue, Lys represents the L-lysine residue, and Val represents the L-valine residue, their enantiomers, diastereoisomers and epimers, as well as their addition salts with a pharmaceutically-acceptable acid or base.

The term amino acid residue denotes an amino acid which lacks a hydrogen atom on the amine function or the hydroxy group of the acid function, or alternatively which lacks both a hydrogen atom on the amine function and the hydroxy group of the acid function.

In general, the rules of peptide nomenclature used in the present invention are in accordance with the 1983 IUPAC-IUB recommendations (*Eur. J. Biochem.*, 138, 9–36, (1984)).

More precisely, the invention relates to compounds of the general formula (I) in which:

$R_1$ represents an amino acid residue having the L or D configuration, the terminal amine of which may or may not be acetylated and which is selected from alanine, cysteine, glycine, histidine, leucine, glutamic acid, glutamine, arginine, asparagine, aspartic acid, lysine, methionine, phenylalanine, proline, serine, threonine, tryptophan, tyrosine, valine and naphthylalanine, $R_2$ represents an amino acid residue having the L or D configuration, the C-terminal function of which is an amide, free acid or alcohol function, the amino acid being selected from alanine, methylalanine, phenylalanine, naphthylalanine, arginine, asparagine, aspartic acid, cysteine, glutamine, glutamic acid, glycine, histidine, leucine, lysine, methionine, proline, hydroxyproline, serine, threonine, tryptophan, tyrosine and valine, $X_1$ and $X_2$ are so selected that the ring of the compounds of the general formula (I) contains 22 atoms; they are dependent and are selected from the following amino acid residues:

| $X_1$ | $X_2$ |
| --- | --- |
| —Glu— | —Dab— |
| —Asp— | —Orn— |
| —homoGlu— | —Dpr— |
| —Dab— | —Glu— |
| —Orn— | —Asp— |
| —Dpr— | —homoGlu— |

—Dab— represents the L-diaminobutyric acid residue, and —Dpr— represents the L-diaminopropionic acid residue, their enantiomers, diastereoisomers and epimers, as well as their addition salts with a pharmaceutically-acceptable acid or base.

Of the pharmaceutically-acceptable acids there may be mentioned by way of non-limiting example hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid, etc.

Of the pharmaceutically-acceptable bases there may be mentioned by way of non-limiting example sodium hydroxide, potassium hydroxide, tributylamine, tert.-butylamine, etc.

The invention relates also to a process for the preparation of the compounds of formula (I), characterised in that they may be obtained by various methods, such as solid-phase sequential synthesis, synthesis of fragments and coupling thereof in solution, enzymatic synthesis, genetic synthesis by cloning and expression of genes in transformed bacteria, or by various combinations of these techniques.

The general methods of solid-phase peptide synthesis have been described by B. W. Erickson and R. B. Merrifield (*"The Proteins"*, Solid-phase Peptide Synthesis, 3rd edition, Volume II, 257–527, (1976)).

Solid-phase synthesis may be effected using an automatic apparatus which carries out, in a repetitive and programmable manner, cycles of deprotections, couplings and washings which are necessary for the sequential introduction of the amino acids into the peptide chain. The amino acid, which is preferably C-terminal, is attached to a resin customarily used for the preparation of polypeptides, preferably a polystyrene cross-linked with the aid of from 0.5 to 3.0% divinylbenzene and provided with activated radicals, such as chloromethylene or hydroxymethylene, which allow the first amino acid to be attached in a covalent manner to the resin. The appropriate choice of resin allows a C-terminal carboxylic acid, amide or alcohol function to be attached.

The choice of coupling site for the fragments is frequently determined in such a manner as to minimise the risks of racemisation. Three possible non-racemising coupling sites are, for example, the C-terminal function of 2-proline, of 3-hydroxyproline and of 4-glycine.

The amino acids are then introduced one by one in the order determined by the operator. Each synthesis cycle corresponding to the introduction of one amino acid comprises deprotection, preferably N-terminal, of the peptide chain, successive washing steps in order to remove the reagents, coupling with activation of the amino acid, and further washings. Each of these operations is followed by filtration which is carried out through sintered glass incorporated into the reactor in which the synthesis is carried out.

The coupling reagents which are used are conventional reagents of peptide synthesis, such as dicyclohexylcarbodiimide (DCC) and hydroxybenzotriazole (HOBt) or benzotriazol-1-yl-oxytris(dimethylamino)phosphonium hexafluorophosphate (BOP) or diphenylphosphorylazide (DPPA). Activation by means of the formation of mixed anhydrides is also possible.

Each amino acid is introduced into the reactor in excess, for example quadruple excess, relative to the degree of substitution of the resin, and in an approximately equivalent amount relative to the coupling agents. The coupling reaction may be checked at each step of the synthesis by means of the Ninhydrin reaction test described by E. Kaiser et al. (*Analyt. Biochem.*, 34, 595–599, (1970)).

After assembly of the peptide chain on the resin, treatment with a strong acid, such as trifluoroacetic acid, or fluorohydric acid in the presence of anisole, ethanedithiol or 2-methylindole, enables the peptide to be separated from the resin and, where appropriate, allows the peptide to be freed of its protecting groups. The compound is then purified by conventional purification techniques, especially chromatographic techniques.

The peptides of the present invention may likewise be obtained by coupling selectively protected peptide fragments in solution, which fragments may be prepared either in the solid phase or in solution. The general methods of peptide synthesis in solution are, for example, described by F. M. Finn and K. Hofmann (*"The Proteins"*, 3rd edition, Volume II, 105–253, (1976), "Synthesis of peptides by solution methods"). The use of protecting groups and the utilisation of their differential stability is analogous to the solid-phase methods, with the exception of the attachment of the peptide chain to the resin. The C-terminal carboxylic group is protected, for example, by a methyl ester or an amide function. The methods of activation at the time of the couplings are likewise analogous to those employed in the solid-phase synthesis.

The compounds of the invention have very valuable pharmacological properties. Studies carried out on the products of the present invention show that they enable the development of a stenosing vascular lesion to be prevented effectively in vivo, in particular as a result of an inhibiting activity on the proliferation component of the vascular smooth muscle cells.

These properties allow the compounds of the present invention to be used as medicaments in the treatment and prevention of atherosclerotic vascular lesions, and in particular for preventing vascular re-stenoses following bypass surgery, vascular, especially coronary, dilatation, or other forms of vascular repermeabilisation, and following heart transplant.

The products of the invention may also be especially useful for preventing and treating vascular alterations associated with arterial hypertension or with diabetes, and especially retinal incidents.

Furthermore, the anti-proliferative activity of the compounds may be used in the treatment of certain cancers and of certain dermatological disorders, such as psoriasis.

The present invention relates also to pharmaceutical compositions containing as active ingredient at least one compound of the general formula (I) or an addition salt thereof with a pharmaceutically-acceptable acid or base, on its own or in combination with one or more inert, non-toxic excipients or carriers.

Of the pharmaceutical compositions according to the invention, special mention may be made of those which are suitable for oral, parenteral or nasal administration, tablets, dragées, sublingual tablets, sachets, paquets, gelatin capsules, glossettes, lozenges, suppositories, creams, ointments, dermic gels, and aerosols.

The dosage varies according to the age and weight of the patient, the nature and severity of the disorder, and the mode of administration.

Administration may be oral, nasal, rectal or parenteral. In general, the dosage ranges from 0.2 to 100 mg for one treatment in one or more doses per 24 hours.

The following Examples illustrate the invention and do not limit it in any way.

EXAMPLE 1

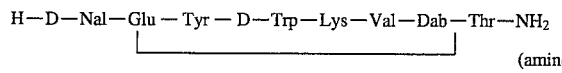

(SEQ ID NO: 2)

(amino bridge)

2 g of an amide resin substituted in an amount of 0.5 mmol/g of resin are treated with 20% piperidine in dimethylformamide (DMF). The actual synthesis is then carried out in accordance with the following repetitive protocol:

| Operation no. | Function | Solvent/reagent | Repetition/time |
|---|---|---|---|
| 1 | washing | DMF | 2 × 2 min. |
| 2 | deprotection | 20% piperidine/DMF | 1 × 5 min. |
| 3 | deprotection | 20% piperidine/DMF | 1 × 15 min. |
| 4 | washing | DMF | 3 × 2 min. |
| 5 | washing | methylene chloride | 3 × 2 min. |
| 6 | coupling | activated protected amino acid | 1 × 90 min. |
| 7 | washing | DMF | 3 × 2 min. |
| 8 | washing | isopropyl alcohol | 3 × 2 min. |
| 9 | washing | methylene chloride | 3 × 2 min. |

The protected amino acids were introduced in the following order:

Fmoc-Thr(But)-OH, Fmoc-Dbu(Boc)-OH, Fmoc-Val-OH, Fmoc-Lys(Z)-OH, Fmoc-D-Trp-OH, Fmoc-Tyr(But)-OH, Fmoc-Glu(OBut)-OH, Fmoc-D-Nal-OH.

The couplings are carried out by dissolving 4 equivalents of the protected amino acid with 4 equivalents of HOBt and 4.4 equivalents of DCC. The solvents used are 30 ml of DMF and 10 ml of methylene chloride.

At the end of the eight cycles corresponding to the sequential attachment of the eight amino acids, the resin is treated with a mixture of trifluoroacetic acid (18 ml), ethanedithiol (1 ml) and anisole (1 ml) for a period of 4 hours at 30° C. The filtrate and the solvents used for washing the resin are combined and evaporated to dryness. The resulting product, of the formula:

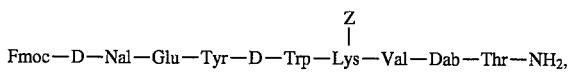

is precipitated in ether.

Cyclisation of the peptide is then carried out in solution in DMF, in the presence of BOP and DIPEA. The mixture is stirred for 12 hours at room temperature. After evaporation of the DMF, the resulting oil is purified on an LH20 column. The cyclised product so obtained:

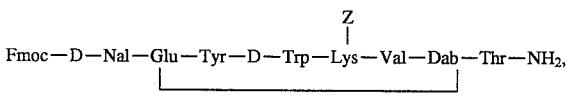

is treated with 20% piperidine in DMF and then subjected to catalytic hydrogenation in a mixture of methanol/water (3/1). The desired product is obtained after purification by inverse phase preparative HPLC ($C_{18}$ column; d=47 mm, length 300 mm), followed by lyophilisation.

Analysis of the peptide is carried out after splitting thereof into amino acids by hydrolysis in 6N hydrochloric acid for 18 hours at 110° C. and quantitative analysis of the amino acids by HPLC.

| Amino acid composition: | | | | | | |
|---|---|---|---|---|---|---|
| | Glu | Thr | Val | D-Nal | Lys | Tyr |
| calculated | 1 | 1 | 1 | 1 | 1 | 1 |
| found | 1.04 | 0.97 | 0.97 | 0.95 | 1.06 | 1.02 |

Dab: not determined; D-Trp: not determined

Mass spectrum (FAB): MH+: m/z=1103.

The following Examples are carried out in accordance with the same process as that described in Example 1.

EXAMPLE 2: H—Ala—Asp—Tyr—D—Trp—Lys—Val—Orn—Ser—NH₂  (SEQ ID NO: 3)

EXAMPLE 3: H—D—Nal-homo-Glu—Tyr—D—Trp—Lys—Val—Dpr—Thr—NH₂  (SEQ ID NO: 4)

EXAMPLE 4: H—D—Nal—Dab—Tyr—D—Trp—Lys—Val—Glu—Ser—NH₂  (SEQ ID NO: 5)

EXAMPLE 5: H—Val—Orn—Tyr—D—Trp—Lys—Val—Asp—Thr—NH₂  (SEQ ID NO: 6)

EXAMPLE 6: H—D—Nal—Dpr—Tyr—D—Trp—Lys—Val-homo-Glu—Ser—NH₂  (SEQ ID NO: 7)

PHARMACOLOGICAL STUDY OF THE COMPOUNDS OF THE INVENTION

EXAMPLE 7

Effects on Myointimal Proliferation Induced by Endothelial Denudation

Male Wistar rats (450–500 g, Charles River) are pretreated subcutaneously with the compound of Example 1 (100 µg/kg/day), or its carrier, during the 2 days preceding endothelial denudation. The daily dose is administered in two batches. After 2 days' pretreatment, the endothelium of the common left carotid is removed by three successive passages of an embolectomy probe (Fogarty 2F, Baxter), and the treatment is continued for 5 days. Fourteen days after endothelial denudation, the rats are anaesthetised with pentobarbital (60 mg/kg i.p.) and the carotids are fixed under pressure (11996 Pa) before being removed. The central portion of each artery is divided into 4 segments, which are enclosed in paraffin. 5 µm transverse sections, which are not serial, are then prepared from each segment and dyed with orcein. The surfaces of the media and of the neointima are measured by means of image analysis (Logiciel Histo, Biocom, Les Ulis). The results are reproduced in Table I below:

|  | I/M % | NEOINTIMA 1000 × µm² |
|---|---|---|
| CARRIER (n = 11) | 133 ± 13 | 160 ± 18 |
| EXAMPLE 1 100 µg/kg s.c. (n = 6) | 66 ± 10 | 75 ± 11 |

Duration of treatment: −2 to +5 days after the lesion. (Total duration: 7 days)
Measurements carried out 14 days after the lesion on the rat carotid
n = number of rats
I/M % = ratio neointima/media

EXAMPLE 8

Effects on the Incorporation of [³H]-Thymidine

Male Wistar rats (Charles River) weighing 300 g are pretreated subcutaneously with the compound of Example 1 (100 µg/kg/day), or its carrier, during the two days preceding endothelial denudation. The daily dose is administered in 2 batches. After 2 days' pretreatment, the endothelium of the animals is removed by the following method. After anaesthesia with methohexital (Brietal, 60 mg/kg i.p.), an embolectomy probe (Fogarty 2F, Baxter) is introduced into the aorta by the carotid route. Removal of the aortal endothelium is carried out by three successive passages of the ballonet probe. The treatment is continued for 3 days.

Three days after endothelial denudation, the rats are sacrificed and the aorta is removed in order to determine the incorporation of [³H]-thymidine. The thoracic aorta is cleaned of the adjacent adipose tissues in Krebs-Henseleit medium having the following composition (in mmol/l): NaCl: 120; KCl: 4.8; CaCl₂: 1.8; KH₂PO₄: 1.4; MgSO₄: 1.2; NaHCO₃: 25; glucose: 5, and bovine albumin serum: 10 g/l; pH: 7.4, carbogen. The vascular preparation is then pre-incubated in that physiological solution for one hour at 37° C. and is then transferred for a period of one hour at 37° C. to a Krebs-Henseleit medium which has the same composition but to which is added [³H]-thymidine (specific activity: 1.48–2.22 TBq/mmol). There follows post-incubation for a period of one hour in a Krebs-Henseleit medium without [³H]-thymidine. After washing in a Tris-EDTA buffer (Tris: 10 mM; EDTA: 10 mM; NaCl: 100 mM), the aorta is stored at −20° C. After defrosting, the intima-media is removed, ground and incubated for 30 minutes in the presence of pronase (type B, nuclease free, 4 mg/ml) and of SDS (5 mg/ml). The homogenate is centrifuged at 2250 g for 10 minutes at 10° C. and the supernatant is divided into 2 fractions, one for analysis of [³H]-DNA, the other for analysis of total DNA.

For analysis of [³H]-DNA, the DNA is coprecipitated by the addition of 13.3 µl of BSA (3 mg/ml of Tris-EDTA) and 1 ml of 20% trichloroacetic acid per ml of supernatant. After 30 minutes at 4° C., the precipitate is filtered through a nitrocellulose membrane (porosity: 45 µm), and the radioactivity is determined by means of a liquid scintillation spectrofluorometer. The quantity of total DNA is determined by spectrofluorimetry using DAPI (4',6-diamidino-2-phenylindole) (100 ng/ml) as fluorescent probe, which inserts itself between the A and T bases of the DNA. The length of the excitation wave is 360 nm and the length of the emission wave is 450 nm. The concentration of DNA is determined relative to a standard range of DNA, and the quantity of DNA contained in the aorta is then calculated, as is the ratio cpm/mg of DNA corresponding to the proliferation index.

The results are reproduced in Table II:

|  | [³H]-THYMIDINE UPTAKE (dpm/µg DNA) | % INHIBITION 1000 × µm² |
|---|---|---|
| CARRIER (n = 17) | 10116 ± 1172 | — |
| EXAMPLE 1 100 µg/kg s.c. (n = 17) | 7568 ± 608 | 25,20% |

Duration of treatment: −2 to +3 days after the lesion. (Total duration: 5 days)
Measurements carried out 3 days after the lesion on the rat carotid

PHARMACEUTICAL COMPOSITION

EXAMPLE 9:
Tablet: Preparation formula for 1000 tablets each containing 2 mg

| | |
|---|---|
| compound of Example 1 | 2 g |
| hydroxypropylcellulose | 2 g |
| corn starch | 10 g |
| lactose | 100 g |
| magnesium stearate | 3 g |
| talc | 3 g |

---

We claim:

1. A compound selected from those of formula (I):

$$R_1-X_1-\text{Tyr-D-Trp}-\text{Lys}-\text{Val}-X_2-R_2 \qquad (I)$$

(with $X_1$ and $X_2$ connected by a bond)

in which:

$R_1$ represents a 3-(2-naphthyl)-D-alanine (D-Nal) residue, $R_2$ represents a threonine (Thr) residue, $X_1$ and $X_2$ are a glutamic acid residue (Glu) and a L-2,4-diaminobutyric acid residue (Dab), respectively which are connected by means of an amide bond and which confer on the ring so formed a number of atoms equal to 22, Tyr represents the L-tyrosine residue, D-Trp represents the D-tryptophan residue, Lys represents the L-lysine residue, and Val represents the L-valine residue, its enantiomers, diastereoisomers and epimers, as well as its addition salts with a pharmaceutically-acceptable acid or base.

2. A method for treating an animal or human living body afflicted with a disease requiring an inhibitor of the proliferation component of vascular smooth muscle cells resulting from atherosclerotic vascular lesions, vascular re-stenosis following bypass surgery, vascular dilation, and heart transplant, vascular alterations associated with arterial hypertension, proliferative diabetic retinopathy, breast, lung and prostate cancers, and psoriasis, comprising the step of administering to said living body an amount of a compound of claim 1 which is effective for alleviation of said disease.

3. A pharmaceutical composition useful as an inhibitor of the proliferation component of smooth muscle cells which contains as active ingredient an effective amount of a compound according to claim 1, in combination with one or more pharmaceutically-acceptable excipients or vehicles.

* * * * *

UNITED STATES PATENT AND TRADEMARK OFFICE
CERTIFICATE OF CORRECTION

PATENT NO. : 5,569,647
DATED : October 29, 1996
INVENTOR(S) : Jean-Luc Fauchere; Christophe Thurieau; Jean-Paul Vilaine; Philip Janiak It is certified that error appears in the above-indentified patent and that said Letters Patent is hereby corrected as shown below:

Column 3, line 40: "Washing" should read -- washing --.

Column 9, last line in column: "(ix) FEATURE:" should be moved to top of Column 11.

Column 13, last line in column: "(ix) FEATURE:" should be moved to top of Column 15.

Signed and Sealed this

Fourth Day of March, 1997

Attest:

BRUCE LEHMAN

Attesting Officer

Commissioner of Patents and Trademarks